US006998118B2

(12) United States Patent
Kaspar et al.

(10) Patent No.: US 6,998,118 B2
(45) Date of Patent: Feb. 14, 2006

(54) TARGETED RETROGRADE GENE DELIVERY FOR NEURONAL PROTECTION

(75) Inventors: Brian K. Kaspar, San Diego, CA (US); Fred H. Gage, La Jolla, CA (US); Daniel A. Peterson, Gurnee, IL (US)

(73) Assignee: The Salk Institute for Biological Studies, La Jolla, CA (US)

( * ) Notice: Subject to any disclaimer, the term of this patent is extended or adjusted under 35 U.S.C. 154(b) by 66 days.

(21) Appl. No.: 10/032,047

(22) Filed: Dec. 21, 2001

(65) Prior Publication Data

US 2003/0118552 A1 Jun. 26, 2003

(51) Int. Cl.
*A61K 48/00* (2006.01)
*C12N 5/22* (2006.01)
*C12N 15/864* (2006.01)

(52) U.S. Cl. .................. 424/93.2; 435/320.1; 435/368; 435/456

(58) Field of Classification Search ............... 424/93.2; 514/44; 435/320.1, 456
See application file for complete search history.

(56) References Cited

U.S. PATENT DOCUMENTS

| | | | | |
|---|---|---|---|---|
| 4,955,892 | A | | 9/1990 | Daniloff ...................... 606/152 |
| 5,092,871 | A | | 3/1992 | Aebischer et al. .......... 606/152 |
| 6,632,427 | B1 | * | 10/2003 | Finiels et al. ............... 424/93.2 |
| 6,800,281 | B1 | * | 10/2004 | Aebischer et al. ......... 424/93.2 |
| 2002/0031493 | A1 | * | 3/2002 | Horellou et al. ........... 424/93.2 |
| 2003/0050273 | A1 | * | 3/2003 | Ozawa et al. ................. 514/44 |

OTHER PUBLICATIONS

Dorlund's Illustrated Medical Dictionary, 28th Edition, W.B. Saunders Co., Philadelphia, PA, 1994, pp. 832, 1131, 1361.*
Peterson et al., "Prophylactic neuroprotection of injured entorhinal cortical neurons by retrograde in vivo gene delivery of an anti-apoptotic transgene," European Journal of Neuroscience 12 (Suppl. 11): 233, Abstract 110.13, Jun. 2000.*
Simon et al., "bcl-2 gene therapy exacerbates exitotoxicity," Human Gene Therapy 10: 1715-1720, Jul. 1, 1999.*
Orkin et al., Report and Recommendations of the Panel to Assess the NIH Investment in Research on Gene Therapy, isssued Dec. 7, 1995 by the US Natl. Inst. of Health, Bethesda, MD.*
Verma et al., "Gene therapy—promises, problems and prospects," Nature 389: 239-242, Sep. 18, 1997.*
Rosenberg et al., "Gene therapist, heal thyself," Science 287: 1751, Mar. 10, 2000.*
Hsich et al., "Critical issues in gene therapy for neurologic disease," Huamn Gene Therapy 13: 579-604, Mar. 20, 2002.*
Zou et al., "Prolonged transgene expression mediated by a helper-dependent adenoviral vector (hdAd) in the central nervous system," Mol. Ther. 20(2): 105-113, Aug. 2000.*
Aebischer & Ridet, Recombinant Proteins for Neurodegenerative Diseases: The Delivery Issue, Trends Neurosciences, 2001 24(9):533-40.
Antonawich et al., BCL-2 Transduction, Using a Herpes Simplex Virus Amplicon, Protects Hippocampal Neurons from Transient Global Ischemia, Academic Press, Experimental Neurology 156, 130-137 (1999).
Bartlett et al., Infectious Entry Pathway of Adeno-Associated Virus and Adeno-Associated Virus Vectors, Journal of Virology, Mar. 2000, p. 2777-2785.
Bartlett et al., Selective and Rapid Uptake of Adeno-Associated Virus Type 2 in Brain, Human Gene Therapy 9:1181-1186 (May 20, 1998).
Blomer et al., BCL-XL Protects Adult Septal Cholinergic Neurons from Axotomized Cell Death, Proc. Natl. Acad. Sci. USA vol. 95, pp. 2603-2608, Mar. 1998.
Calamandrei and Alleva, Neuronal Growth Factors, Neurotrophins and Memory Deficiency, Behav Brain Res 1995 Jan 23;66(1-2):129-32.
Carver and Barness, Trophic Factors for the Gastrointestinal Tract, Clin Pernatol (1996) 23(2):265-85.
Cleveland et al., From Charcot to SOD1: Mechanisms of Selective Motor Neuron Death in ALS, Neuron, vol. 24, 515-520, Nov., 1999.
DeFalco et al., Virus-Assisted Mapping of Neural Inputs to a Feeding Center in the Hypothalamus, *Science* 291:2608-2613 (Mar. 2001).
Dolorfo & Amaral, Entorhinal Cortex of the Rat: Topographic Organization of the Cells of Origin of the Perforant Path Projection to the Dentate Gyrus, The Journal of Comparative Neurology 398:25-48 (1998).
Duvoisin, Roger C., Overview of Parkinson's Disease, Annals New York Academy of Sciences,pp. 187-193.
Fawcett J.W., Spinal Cord repair: From Experimental Models to Human Application, Spinal Cord (1998) 36(12): 811-7.
Gomez-Isla et al., Profound Loss of Layer II Entorhinal Cortex Neurons Occurs in Very Mild Alzheimer's Disease, The Journal of Neuroscience, Jul. 15, 1996, 16(14):4491-4500.

(Continued)

*Primary Examiner*—Scott D. Priebe
(74) *Attorney, Agent, or Firm*—Klarquist Sparkman, LLP

(57) ABSTRACT

Methods are disclosed for transducing neurons with heterologous genes using retrograde viral transport. The methods disclosed employ substantially non-toxic vectors, such as adeno-associated virus vectors, that are capable of retrograde axonal transport to introduce and express genes in the neurons. This method has applications in the mapping of neural pathways, in stimulating or inhibiting the growth of neurons, and in the treatment of various neurodegenerative diseases such as Alzheimer's disease, Parkinson's disease, and amyotrophic lateral sclerosis.

6 Claims, No Drawings

OTHER PUBLICATIONS

Gonzalez-Garcia, BXL-X is Expressed in Embryonic and Postnatal Neural Tissues and Functions to Prevent Neuronal Cell Death, Proc. Natl. Acad. Sci, USA, vol. 92, pp. 4304-4308, May 1995.

Hefti et al., Development of Neurotrophic Factor Therapy for Alzeheimer's Disease, Ciba Found Symp. (1996)196: 54-69.

Kishi & Cowan, A Quantitative EM Autoradiographic Study of the Commisural and Associational Connections of the Dentate Gyrus in the Rat, Anat. Embryol. 160, 173-186 (1980).

Koliatsos V.E., Biological Therapies for Alzheimer's Disease: Focus on Trophic Factors, Crit Rev Neurobiol (1996) 10(2):205-38.

Latchman & Coffin, Viral Vectors for Gene Therapy in Parkinson's Disease, Rev Neurosci. (2001) 12(1):69-78.

Monahan & Samulski, AA V Vectors: is Clinical Success on the Horizon?, Gene Therapy (2000) 7, 24-30.

Monahan & Samulski, Adeno-Associated Virus Vectors for Gene Therapy: More Pros than Cons?, Mol Med Today. (2000) 6(11):433-40.

Offen et al., Apoptosis as a General Cell Death Pathway in Neurodegenerative Diseases, J Neural Transm Suppl. (2000) 58:153-66.

Peterson et al., Central Neuronal Loss and Behavioral Impairment in Mice Lacking Neurotrophin Receptor p75, The Journal of Comparative Neurology 404:1-20 (1999).

Qing et al., Human Fibroblast Growth Factor Receptor 1 is a Co-Receptor for Infection by Adeno-Associated Virus 2, Nature Medicine, vol. 5, No. 1, pp. 71-77, Jan. 1999.

Senut et. al., Intraneuronal Aggregate Formation and Cell Death after Viral Expression of Expanded Polyglutamine Tracts in the Adult Rat Brain, *J Neurosci.* Jan. 1, 2000; 0(1):219-229.

Smith-Arica & Bartlett, Gene Therapy: Recombinant Adeno-Associated Virus Vectors, Curr Cardiol Rep. (2001) 3(1):43-9.

Snyder, et al. Effective and Stable Adeno-Associated Virus-Mediated Transduction in the Skeletal Muscle of Adult Immunocompetent Mice, *Hum Gene Ther.* Nov. 1, 1997; 8(16):1891-900.

Summerford et al., $\alpha V \beta 5$ Integrin: a Co-Receptor for Adeno-Associated Virus Type 2 Infection, Nature Medicine, vol. 5, No. 1, pp. 78-82, Jan. 1999.

Terenghi G., Peripheral Nerve Regeneration and Neurotrophic Factors, J Anat (1999) 194 ( Pt 1):1-14.

Yamada et al., Herpes Simplex Virus Vector-Mediated Expression of BCL-2 Prevents 6-Hydroxydopamine-Induced Degeneration of Neurons in the Substantia Nigra *in Vivo,* Proc. Natl. Acad. Sci., vol. 96, pp. 4078-4083, Mar. 1999.

Yuen EC, The Role of Neurothrophic Factors in Disorders of Peripheral Nerves and Motor Neurons, Phys Med Rehabil Clin N Am. (2001) 12(2):293-306, viii.

Yuen et al., Therapeutic Potential of Neurotrophic Factors for Neurological Disorders, Am. Neurol. (1996) 40(3):346-54.

Xiao et al., Production of High-Titer Recombinant Adeno-Associated Virus Vectors in the Absence of Helper Adenovirus, Journal of Virology, Mar. 1998, p. 2224-2232.

Xiao et al., Gene Transfer by Adeno-Associated Virus Vectors into the Central Nervous System, Experimental Neurology 144, 113-124 (1997).

Peel, et al. 2000. Adeno-associated virus vectors: Activity and applications in the CNS. *Journal of Neuroscience Methods,* 98:95-104.

Mellecamps, S. et al. Synaptic Sprouting Increases the Uptake Capacities of Motoneurons in Amyotrophic Lateral Sclerosis Mice. Proced. Nat. Acad. Sci. Jun. 19, 2001, vol. 98, No. 13, pp. 7582-7587.

Chamberlin, N. L. et al. Recombinant Adeno-Associated Virus Vector: Use for Transgene Expression and Anterograde Tract Tracing in the CNS. Brain Research. 1998, vol. 793, pp. 169-175.

Bjorklund, A. et al. Towards a Neuroprotective Gene Therapy for Parkinson's disease: Use of Adenovirus, AAV and Lentivirus Vectors for Gene Transfer of GDNF to the Nigrostriatal System in the Rat Parkinson Model. Brain Research. 2000, vol. 886, pp. 82-98.

Kaplitt, M. G. et al. Long-Term Gene Expression and Phenotypic Correction Using Adeno-Associated Virus Vectors in the Mammalian Brain. Nature Genetics. Oct. 1994, vol. 8, pp. 148-154.

Skorupa, A. F. et al. Sustained Production of Beta-Glucuronidase from Localized Sites After AAV Vector Gene Transfer Results in Widespread Distribution of Enzyme and Reversal of Lysomal Storage Lesions in a Large Volume of Brain in Mucopolysaccharidosis VII Mice. Experimental Neurology. 1999, vol. 160, pp. 17-27.

\* cited by examiner

TARGETED RETROGRADE GENE DELIVERY FOR NEURONAL PROTECTION

STATEMENT OF GOVERNMENT SUPPORT

This invention was made with United States government support pursuant to grant number AG-10435 from the National Institutes of Health; the United States government has certain rights in the invention.

BACKGROUND OF THE INVENTION

1. Field of the Invention

The present invention relates to a method for transducing neurons with heterologous genes using retrograde viral transport. In greater detail, the present invention relates to a method for introducing and expressing genes in neurons using an adeno-associated virus vector that is capable of retrograde axonal transport. This method has applications in mapping neural pathways, in stimulating or inhibiting the growth of neurons, and in treating various neurodegenerative diseases.

2. Background Art

Diseases of the central nervous system (CNS), more particularly, neurodegenerative diseases, often manifest themselves as a result of the loss or dysfunction of specific projection neurons. Examples include the loss of dopaminergic nigrostriatal projection neurons in Parkinson's disease, entorhinodentate projection neurons in Alzheimer's disease, and spinal motorneurons in amyotrophic lateral sclerosis. See, also, Mark Paul Mattson, Pathogenesis of Neurodegenerative Disorders (Contemporary Neuroscience) (Humana Press; 2001); Marie-Francoise Chesselet (Editor), Molecular Mechanisms of Neurodegenerative Diseases, 1st edition (Humana Press, 2001); Hyman M. Schipper (Editor), Astrocytes in Brain Aging and Neurodegeneration, 1st edition (R G Landes Co., 1998), and the like (each herein incorporated by reference).

Molecular approaches to treat such diseases have opened up new avenues for clinical intervention and assisted scientific study of disease mechanisms. Diseases with a monogenetic etiology may be treated by inserting the gene encoding for the deficient protein. An alternative therapeutic approach for degenerative disorders that may be polygenetic, or that represent the convergence of several risk factors, is to interrupt a common pathway for cell vulnerability. Candidates for this approach include anti-apoptotic genes, such as members of the ras or Bcl-2 family, or molecules such as CGP 3466B, to disrupt the apoptotic cascade and prevent cell death. Neurodegenerative processes are generally characterized by the long-lasting course of neuronal death and the selectivity of the neuronal population or brain structure involved in the lesion. Two main common forms of cell death that have been described in neurons as in other vertebrate tissues i.e., necrosis and apoptosis. Necrosis is the result of cellular "accidents", such as those occurring in tissues subjected to chemical trauma. The necrotizing cells swell, rupture and provoke an inflammatory response. Apoptosis, on the other hand, is dependent on the cell's "decision" to commit suicide and die, and therefore is referred to as "programmed cell death" (PCD). The course of apoptotic death is characterized by a massive morphological change, including cell shrinkage, nuclear (chromosome) condensation and DNA degradation. Activation of PCD in an individual cell is based on its own internal metabolism, environment, developmental background and its genetic information. Such a situation occurs in most of the neurodegenerative disorders such as Alzheimer's, Parkinson's and Huntington's diseases and amyotrophic lateral sclerosis (ALS). In these pathological situations, specific neurons undergo apoptotic cell death characterized by DNA fragmentation, increased levels of pro-apoptotic genes and "apoptotic proteins" both, in human brain and in experimental models. It is of utmost importance to conclusively determine the mode of cell death in neurodegenerative diseases, because new "anti-apoptotic" compounds may offer a means of protecting neurons from cell death and of slowing the rate of cell degeneration and illness progression (see, e.g., Offen et al., J Neural Transm Suppl. (2000) 58:153–66).

However, one problem involved in using such in vivo genetic approaches to effectively treat diseases of the CNS is that the CNS has a heterogeneous cytoarchitecture. For example, intracranial injection must deliver the vector to a specific location without damaging the targeted cells or causing collateral infection of nearby cells. This precision of delivery is difficult to achieve since many target neuronal populations are physically intermixed with many different neurons. In addition, many target neuronal populations are effectively inaccessible using current delivery methods.

The development of the adeno-associated virus (AAV) vector, which is capable of infecting post-mitotic neurons, has greatly facilitated in vivo gene delivery to the central nervous system (CNS). Gene therapy vectors based on the adeno-associated virus (AAV) are being developed for a widening variety of therapeutic applications. Enthusiasm for AAV is due, not only to the relative safety of these vectors, but also to advances in understanding of the unique biology of this virus. Wild-type AAV is a nonpathogenic parvovirus that is incapable of replication without the co-infection of a helper virus, such as adenovirus or HSV. When used as a vector, almost all of the AAV genome is deleted, leaving only terminal repeats with DNA replication and packaging signals. This removal of the viral coding sequence prevents the generation of wild-type helper virus and reduces the possibility of immune reactions caused by undesired viral gene expression. It is also possible to remove populations of contaminating helper virus from the AAV vector population on the basis of structurally distinct coat proteins.

AAV is capable of transducing both dividing and nondividing cells, and is thus of particular applicability to the CNS, where most of the cells are nondividing. AAV is an integrating virus and the integrated provirus is very stable, thus offering long-term transduction; there have been reports of stable gene expression for up to two years after AAV-mediated gene delivery. Lastly, in contrast to other viral vectors such as adenovirus, which induce severe immune responses, AAV vectors characteristically exhibit no cellular immune response against vector-transduced cells. In sum, AAV is particularly attractive due to its low toxicity and immunogenicity and its long-term gene expression.

AAV vectors were previously thought to be of use only in the transduction of local neurons and anterograde axon tracing. For example, Chamberlin et al. found that in contrast to other viral vectors that may be retrogradely transported by neurons in remote regions of the brain, the AAV appeared to transduce only local neurons (N. Chamberlin et al., *Brain Research* 793:174 (1998)). In addition to AAV, DeFalco et al. report the use of the pseudorabies virus to trace the locations of selected neurons (DeFalco et al., Virus-Assisted Mapping of Neural Inputs to a Feeding Center in the Hypothalamus, *Science* 291:2608–2613 (March 2001)).

Such retrograde transport has been reported for herpes simplex (HSV), adenovirus, and pseudorabies virus. However, viral toxicity from these vector systems can limit expression duration and yield variable results. Viruses used as vectors in this manner generally carry deletions in viral genes, either in order to limit viral toxicity or to make the viruses unable to replicate. However, although some viral genes are inactivated in these vectors, many functional viral genes are present, which may make the vectors toxic or reactivate latent viruses in recipient cells. Even so-called "defective viral vectors," which have been produced from HSV and the like and which contain no viral genes at all, still present problems with continued gene expression, pathogenicity, and reversion to wild type. Additionally, such vectors, such as adenovirus vectors, often have capsid proteins that provoke a strong immune response. To date, retrograde axonal transport has not been accomplished with a substantially nontoxic genetic vector. As used herein, what is meant by a "substantially nontoxic genetic vector" is a vector which is not directly toxic to transfected cells and which does not cause a post-transfection immune response. Such a substantially non-toxic, retrograde vector delivery system would be of great use in the mapping of CNS circuitry and in the treatment of the various neurodegenerative illnesses described above.

Thus, what is needed in the art is an efficient mechanism for delivering heterologous genes to neuronal cells. Tackling neurodegenerative diseases represents a formidable challenge for our ageing society. Recently, major achievements have been made in understanding the molecular mechanisms responsible for such diseases, and, simultaneously, numerous proteins such as neurotrophic factors, anti-apoptotic or anti-oxidant have been identified as potential therapeutic agents. Although many neurotrophic factors have been tested on individuals suffering from various neurodegenerative disorders, to date none has shown efficacy. Inadequate protein delivery is believed to be part of the problem. Recent improvements in pump technology, as well as in cell and gene therapy, are providing innovative ways to allow localized, regulatable delivery of proteins in brain parenchyma, opening new avenues for clinical trials in the not so distant future (see, e.g., Aebischer & Ridet, Trends Neurosci. 2001 24(9):533–40 (generally describing therapeutic genes and methods, incorporated by reference herein). The invention described herein provides such a mechanism.

SUMMARY OF THE INVENTION

One embodiment of the invention is a method for transducing a neuron with a heterologous gene, wherein said neuron has a synaptic portion and a cellular portion. This method includes providing a viral vector comprising a heterologous gene to be transduced into a neuron; and contacting the synaptic portion of said neuron with said viral vector under conditions whereby said contacting results in transduction of the viral vector into said synaptic portion, and retrograde movement of said viral vector from the synaptic portion to the cellular portion, wherein said heterologous gene is incorporated into the genome of the neuron. In some method embodiments, said gene is expressed by said neuron for at least two months. In other method embodiments, said gene is expressed by said neuron for at least four months.

Another embodiment of the invention includes a method for increasing proliferation of a nerve cell, wherein said nerve cell has a synaptic portion and a cellular portion. This method includes the steps of providing a viral vector comprising a growth factor gene to be transduced into said nerve cell; contacting the synaptic end of said nerve cell with said viral vector under conditions whereby said contacting results in transduction of the viral vector into said synaptic end, and retrograde movement of said viral vector from the synaptic end to the cellular end of said nerve cell; and incubating said nerve cell under conditions whereby said growth factor gene is expressed by said nerve cell.

Yet another embodiment of the invention is a method for treating a neurodegenerative disease in a human, that provides the steps of: identifying a human patient in need of treatment for said neurodegenerative disease; providing a viral vector comprising a therapeutic gene to be transduced into a synaptic end of said target neurons of said patient and introducing said viral vector into a terminal field of said target neurons of said patient under conditions whereby said contacting results in transduction of the viral vector into the synaptic end of said target neurons, and wherein said viral vectors migrate from the synaptic end to the cellular end of said target neurons.

DETAILED DESCRIPTION

Embodiments of the invention relate to methods for stably transfecting neuronal cells through retrograde transport of viral particles through the axon to the nucleus. By administering the proper dose of viral vectors carrying a gene of interest to a particular site, it was discovered that these vectors were capable of retrograde transport and stable transfection of the neuron. Herein, what is meant by "retrograde transport" is uptake of the vector at the axon terminal, and transport through the axon in a direction opposite to the direction of propagation of action potentials (and thus "retrograde") and into the body of the neuron in which the viral particles enter the nucleus, underwent single strand synthesis, and became transcriptionally and translationally active.

Such delivery is advantageous in many cases in which the projection neurons themselves are inaccessible, but their terminal projection fields, which define the neurons, are available for delivery of the genetic vector. Successful delivery to such a terminal projection field of a genetic vector capable of retrograde transport would thus result in retrograde transport and infection of the vulnerable projection neurons. In addition to delivering therapeutic transgenes, the identification of such viral transport mechanisms may advance study of CNS circuitry by combining neural tracing with functional modulation of targeted populations resulting from expression of experimental transgenes to effect a gain or loss of function.

Embodiments of the invention involve delivery of a substantially non-toxic, recombinant adeno-associated virus vector having a heterologous gene of interest in order to provide retrograde gene delivery with stable gene expression. Such a vector can be employed in retrograde gene mapping if a marker gene is packaged in the vector. Alternatively, such a vector can be used for the retrograde delivery of a therapeutic gene, such as a growth factor, an anti-apoptotic gene, or an antisense gene. Such therapeutic use would be especially advantageous where the target neuron population is distributed or difficult to reliably access, such as in the central nervous system. For example, therapeutic gene-bearing vectors can be delivered to the hippocampus or striatum, which results in the infection of projection neurons in the entorhinal cortex and the substantia nigra. This demonstrates a targeted delivery strategy of potential use for gene therapy of neurodegenerative diseases, such as Alzheimer's and Parkinson's diseases. Furthermore, an anti-apoptotic gene such as Bcl-xL can be delivered in vivo to a pathway-specific projection neuron population and the retrograde transport, infection, and expression of this gene product can protect these targeted neurons from subsequent injury. Neuroprotective (antiapoptotic) signaling pathways involving neurotrophic factors, cytokines and "conditioning responses" can counteract the effects of aging and genetic predisposition in neurodegenerative disorders. Thus, targeted delivery of anti-apoptotic genes to vulnerable projection neurons may be a useful neuroprotective strategy for early stages of neurodegenerative disease.

By greatly increasing the viral titer at the point of delivery, it was possible to effect retrograde stable transduction of neurons projecting to the delivery field of the AAV vector. This retrograde transport is thought to be mediated by the microtubules of the axon after uptake of the AAV vector at the axon terminal.

It should be noted here that the way in which viral titers are measured in the literature is not standardized. One method involves simply assessing the number of virions containing the viral genome, regardless of infectivity or functionality, using DNA dot blot, Southern blot, or semi-quantitative PCR. These numbers are generally reported as "particles/ml." An assessment of the viral titer using an infectious center assay, in which the rAAV is infected into cells with sufficient helper virus (wild-type AAV and adenovirus) to allow rAAV amplification, provides the number of infectious and replication-competent rAAV particles. This number is generally reported as "infectious units (or infectious particles)/ml." Lastly, an assessment of the viral titer using a rAAV transgene functional assay, which assesses specific transgene expression, provides the number of "transducing units/ml."

Previous experimental use of recombinant AAV vectors have involved relatively low viral titers and have assessed infection of local neurons or anterograde neuronal tracing only. In contrast, embodiments of the invention include methods of raising the virus titer at the point of delivery to preferably $1 \times 10^7$ infectious particles, or more preferably $1 \times 10^8$ infectious particles or more, and most preferably $1 \times 10^9$ infectious particles or more. By using these titer levels, it was possible to detect retrograde transduction of neurons projecting to the delivery field of the AAV vector. Thus, by using a marker gene we were able to identify the nucleus, cell body, and projections for each nerve cell that projected into a predetermined location.

Embodiments of the invention, however, are not necessarily limited to the use of AAV vectors. Any genetic vector may be used to practice the methods disclosed in this application. Of course, the vector should be substantially nontoxic to the transduced cells and enable stable, long-term gene expression. Such vectors may include, for example, lentivirus vectors, liposomal vectors, and the like (see, e.g., Latchman & Coffin, Rev Neurosci. (2001) 12(1):69–78, incorporated by reference herein).

In addition, it is possible to improve the qualities of the rAAV vector by methods well-known in the art, such as chemical modification of the AAV virion structure or capsid gene shuffling. Such methods may be employed to develop AAV strains with new tropism, such as tropism towards axon terminal receptors, as well as strains resistant to naturally occurring neutralizing antibody. Such methods are well within the capabilities of those of ordinary skill in virology.

In accordance with yet another embodiment of the present invention, there are provided methods of treating a neurological disease (including injuries, dysfunctions and disorders) in a mammal comprising administering a therapeutically effective amount or an effective amount of invention vectors as described herein. The present invention concerns the therapeutic application of vectors as described herein to enhance survival of neurons and other neuronal cells in both the central nervous system and the peripheral nervous system. The ability of vectors as described herein to regulate neuronal differentiation and survival during development of the nervous system and also in the adult state indicates that vectors as described herein can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of invention vectors to the treatment of (prevention and/or reduction of the severity of) neurological conditions deriving from injuries, diseases or disorders, including: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system, including Alzheimer's disease; (iii) chronic neurodegenerative diseases of the nervous system, including Parkinson's disease, Huntington's chorea, amylotrophic lateral sclerosis, and the like, as well as spinocerebellar degenerations; (iv) chronic immunological diseases of the nervous system or affecting the nervous system, including multiple sclerosis; (v) disorders of sensory neurons as well as degenerative diseases of the retina; and the like.

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function.

Further disease conditions contemplated for treatment in accordance with the invention include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia, astrocytomas, and the like. Further examples of disorders include Alzheimer's disease, Amyotrophic Lateral Sclerosis (ALS) and Parkinson's disease.

Many neurological disorders are associated with degeneration of discrete populations of neuronal elements and may be treatable with a therapeutic regimen which includes vectors as described herein. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. For example, Huntington's disease involves the degeneration of intrastriatal and cortical cholinergic neurons and GABAergic neurons (see, e.g., Hefti et al., Ciba Found Symp. (1996)196:54–69; Koliatsos V. E., Crit Rev Neurobiol (1996) 10(2):205–38). Pick's disease is a severe neuronal degeneration in the neocortex of the frontal and anterior temporal lobes, sometimes accompanied by death of neurons in the striatum. Treatment of patients suffering from such degenerative conditions can include the application of vectors as described herein, in order to manipulate, for example, the de-differentiation and apoptosis of neurons which give rise to loss of neurons. In preferred embodiments, the vectors as described herein are stereotactically provided within or proximate the area of degeneration.

In addition to degenerative-induced dementias, a preparation of invention vectors can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of invention vectors can be used to treat a restricted form of cerebellar cortical degeneration involving the anterior lobes (vermis and leg areas) such as is common in alcoholic patients.

Other forms of neurological impairment can occur as a result of neural degeneration, such as amyotrophic lateral sclerosis and cerebral palsy, or as a result of CNS trauma, such as stroke and epilepsy. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of invention vectors prevents and/or reverses motor neuron degeneration in ALS patients.

In addition to neurodegenerative diseases, acute brain injuries often result in the loss of neural cells, the inappropriate functioning of the affected brain region, and subsequent behavior abnormalities. Probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis.

The vectors of the present invention can also be used in the treatment of autonomic disorders of the peripheral nervous system, which include disorders affecting the innervation of smooth muscle and endocrine tissue (such as glandular tissue). For instance, invention vectors may be useful to treat tachycardia or atrial cardiac arrythmias which may arise from a degenerative condition of the nerves innervating the striated muscle of the heart.

In addition, invention vectors may be employed to support, or alternatively, antagonize the survival and reprojection of several types of central and peripheral ganglionic neurons, sympathetic and sensory neurons, as well as motor neurons (See, e.g., Terenghi G., J Anat (1999) 194 (Pt 1):1–14). To illustrate, such therapeutic vectors may be useful in treatments designed to rescue, for example, retinal ganglia, inner ear and accoustical nerves, and motorneurons, from lesion-induced death as well as guiding reprojection of these neurons after such damage. Such diseases and conditions include CNS trauma, infarction, infection (such as viral infection with varicella-zoster), metabolic disease, nutritional deficiency, toxic agents (such as cisplatin treatment), and the like. Moreover, certain of the vectors described herein (probably antagonistic forms) may be useful in the selective ablation of sensory neurons, for example, in the treatment of chronic pain syndromes.

Accordingly, there are provided methods of treating neuronal trauma in a mammal comprising administering a therapeutically effective amount of invention vectors as described herein. As used herein, the term "Neuronal trauma" refers to any injury to neuronal tissue produced by an exogenous event such as, for example, blunt force or other sudden physical impact that results in neuronal injury or death, either directly or through the abnormal release by dying neurons of toxic levels of endogenous neurotransmitters or metabolites thereof, e.g., glutamate. Neuronal trauma also refers to decreased neurotransmitter production, or a compromise in neuronal function (See, e.g., Fawcett J. W., Spinal Cord (1998) 36(12):811–7).

The vectors of the present invention can also be used in nerve prostheses for the repair of central and peripheral nerve damage. In particular, where a crushed or severed axon is entubulated by use of a prosthetic device, invention vectors can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains invention vectors.

In yet another embodiment, invention vectors can be used in the treatment of neoplastic or hyperplastic transformations, particularly of the central nervous system and lymphatic system. For instance, certain trophic factors are known to have mitotic or apoptotic activity. Thus, certain invention vectors are capable of inducing differentiation of transformed neuronal cells to become post-mitotic or possibly apoptotic. Treatment with certain invention vectors may involve disruption of autocrine loops, such as TGF-beta or PDGF autostimulatory loops, believed to be involved in the neoplastic transformation of several neuronal tumors. Invention vectors may, therefore, be of use in the treatment of, for example, malignant gliomas, medulloblastomas, neuroectodermal tumors, and ependymonas.

Yet another aspect of the present invention concerns the application of the discovery that invention vectors are likely induction signals involved in other vertebrate organogenic pathways in addition to neuronal differentiation as described above, having potential roles in other ectodermal patterning, as well as both mesodermal and endodermal differentiation processes. Thus, it is contemplated that invention vectors can also be utilized for both cell culture and therapeutic methods involving generation and maintenance of non-neuronal tissue, such as in controlling the development and maintenance of tissue from the digestive tract, liver, lungs, and other organs which derive from the primitive gut, as well as dorsal mesoderm-derived structures including muscular-skeletal tissues and connective tissue of the skin; intermediate mesoderm-derived structures, such as the kidney and other renal and urogenital tissues; and head mesenchymal and neural crest-derived tissue, such as cephalic connective tissue and skull and branchial cartilage, occular tissue, muscle and cardiac tissue (see, e.g., Carver and Barness, Clin Perinatol (1996) 23(2):265–85). This should not be construed as a comprehensive list, and other tissues and diseases that may be affected by the invention vectors are envisaged. For example, memory loss or memory enhancement is encompassed as a potential target for invention vectors (see, e.g., Calamandrei and Alleva Behav Brain Res 1995 Jan. 23; 66(1–2):129–32). Those of skill in the art will readily recognize additional applications of invention vectors based on the components of the invention vectors, e.g., the activities and, thus, the applications of trophic factors (which have been well characterized and are known to those of skill in the art (Yuen et al., Ann Neurol. (1996) 40(3): 346–54)).

1. Production of Viral Vectors

In one experiment, an AAV vector carrying a green fluorescent protein (GFP) reporter gene, or a GFP gene fused to a gene encoding the Bcl-xL anti-apoptotic factor, was produced in the following manner. Recombinant AAV-2 carrying eGFP (available from Clontech, Cambridge, UK) or a GFP-Bcl-xL fusion (human Bcl-xL cDNA, obtained from J. Reed, Burnham Inst.) driven from the human CMV promoter was produced in HEK293 cells by calcium phosphate transient transfection of vector plasmid and pAAV/Ad8 helper plasmid, followed by infection with adenovirus dl312 (MOI 2.0). Virus was purified by two CsCl density gradients, dialysis, and heating to 56° C. for 1 hour. Recombinant virus titers were approximately $5 \times 10^{10}$ infectious particles per milliliter. All viral stocks were tested and found to be free from contaminating adenovirus. More information on these methods can be found in Senut et. al., *J Neurosci.* 2000 Jan. 1; 0(1):219–229. In addition, examples of methods for performing viral titers can be found in Snyder, et al. *Hum Gene Ther.* 1997 Nov. 1; 8(16):1891–900. A general review of biology, immunology and production of AAV can be found in, for example, Monahan & Samulski, Mol Med Today. (2000) 6(11):433–40, and Smith-Arica & Bartlett, Curr Cardiol Rep. (2001) 3(1):43–9 (each incorporated herein by reference).

2. Expression of Reporter Gene Following Viral Injection into Projection Fields

To test the hypothesis that therapeutic or experimental genes can be delivered to projection neurons by retrograde transport of viral particles, AAV containing GFP produced in the manner described above was injected into the hippocampus and striatum of rats. Specifically, F344 female rats (140–160 g; Harlan Sprague-Dawley) were deeply anesthetized and positioned in a stereotaxic frame for right-unilateral injection into the hippocampus (AP–4.0, ML–3.0, and DV–2.5 from dura) or striatum (AP+0.2, ML–3.0, and DV–4.0 from dura). Viral suspension (3 µl per site at $5 \times 10^{10}$ infectious particles/ml) was injected at a rate of 0.3–1.0 µl/min. Animals received either rAAV-GFP (hippocampus, n=12; striatum, n=6) or rAAV-Bcl-xL/GFP (hippocampus, n=12). Animals were transcardially perfused four weeks after viral injection with 4% paraformaldehyde and serial 50 µm thick horizontal sections (hippocampal-injected animals) or coronal sections (striatal-injected animals) by produced by freezing sliding microtomy.

Multiple immunofluorescent labeling used antibodies against NeuN (mouse, 1:50, R. Mullen, Univ. Utah), tyrosine hydroxylase (TH, rabbit, 1:1000, Chemicon), anti-GFAP (guinea pig, 1:1000, Advanced Immunochemical), anti-CD4 and CD8 (both mouse, 1:1000, Pharmingen), and anti-GFP (rabbit, 1:500, Clontech) to enhance detection of the reporter gene. Donkey anti-species antibodies conjugated to biotin, FITC, Cy3, or Cy5 and Streptavidin-FITC (1:250; all from Jackson Immunoresearch) were used for detecting primary antibodies. Fluorescent DNA stains used were DAPI (30 ng/ml), propidium iodide (PI, 1:1000), or ToPro3 (1:5000, all from Molecular Probes). Microscopy was performed using confocal microscopes (BioRad MRC1024UV or Olympus FluoView 200).

Within two weeks following this intrahippocampal injection of rAAV-GFP, there was robust expression of gene product in neurons of all hippocampal subfields with the greatest concentration of GFP-positive neurons in the dentate hilus. We discovered that there was anterograde GFP filling of hippocampal neurons, demonstrating neurotropic infection by AAV. Unilateral injection of AAV-GFP into the right hippocampus was found to infect neurons, as detected by antibodies against the neuronal marker NeuN (red), in all hippocampal subfields.

The GFP gene product (green) was found to fill neuronal cell bodies and anterogradely fill axonal processes, including commissural projections. The location of the perforant pathway lesion was also indicated. Infection was found in Area CA1 neurons, dentate granule neurons, and Area CA3 neurons. In addition, we discovered anterograde filling of hippocampal commissural projections to the non-injected hemisphere. Moreover, there was little infection of dentate granule neurons.

Infection of neurons was also demonstrated by the anterograde filling of processes with diffused GFP. Hilar mossy cells of the hippocampus project to the molecular layer of both the ipsilateral and contralateral granule cell layer, and, accordingly, GFP filled both ipsilateral and contralateral projections. There was little or no host immune response against the virus or GFP transgene, based on the absence of GFAP hypertrophy or of CD4/CD8-positive cells, nor was vascular cuffing observed.

The hippocampal formation receives input from various cortical, subcortical, and commissural projections. Preliminary observations of labeled projection neurons from these regions led the present inventors to a systematic evaluation of retrograde infection and transport following AAV delivery. Cortical input to the hippocampus arises from primarily glutamatergic projection neurons in layer II of the entorhinal cortex traveling via the perforant pathway to form the entorhinodentate projection. Within two weeks of rAAV-GFP delivery to the hippocampus, GFP was expressed in entorhinal layer II neurons. Intrahippocampal injection of AAV-GFP specifically infected entorhinal cortex projection neurons to the dentate gyrus in layer II (ECL2). Expression levels varied between individual layer II neurons; however, three-dimensional sampling using confocal microscopy revealed that more than 80% of layer II neurons expressed some GFP. The distribution and variable intensity of GFP-expression was similar to that which has been reported following intrahippocampal injection of a retrograde tracing dye.

Retrograde infection of projection neurons was less robust among other populations projecting to the AAV-injected hippocampus. Despite commissural projection of dentate hilar neurons to the contralateral dentate molecular layer, few hilar neurons in the contralateral hippocampus expressed GFP. We found that the dentate gyrus contralateral to the site of intrahippocampal AAV-GFP injection showed all cells labeled by propidium iodide (PI, red) and commissural projections filled with GFP (green). There were also few GFP-positive neurons from the subcortical projections to the hippocampus arising from the medial septum, which demostrated retrograde infection of medial septum projection neurons following intrahippocampal AAV-GFP injection.

To determine if retrograde infection was unique to hippocampal projections, AAV-GFP was injected into the striatum followed by examination of projection neurons within the substantia nigra pars compacta for expression of GFP. As described above, the dopaminergic nigrostriatal projection provides important modulatory input to the striatum and the progressive degeneration of this pathway produces the clinical manifestations of Parkinson's disease. As observed in the hippocampus, delivery of AAV in the striatum produced substantial infection of local neurons. Within two weeks of injection to the striatum, there was robust expression of GFP in tyrosine hydroxylase-positive neurons of the substantia nigra pars compacta. No GFP expression was detected in the cerebral cortex of striatal AAV-injected animals, suggesting that retrograde infection from this delivery site may be specific to the nigrostriatal projection.

3. Confirmation of Infection by Viral Particles with Fluorescent Marker

To discriminate between retrograde transport of GFP protein and true infection of projecting neurons by retrogradely transported AAV viral particles, AAV particles conjugated to the fluorescent dye, Cy3, were injected into either the hippocampus or striatum. This was accomplished in the following manner.

For viral transport studies, rAAV-GFP was produced with pXX6, a helper plasmid for use in adenovirus-free AAV packaging, purified by four CsCl gradients to ensure high purity, and labeled with N-hydroxysuccinimidyl ester Cy3 reagent (Amersham). Animals received intracranial injection of Cy3-conjugated AAV (hippocampus, n=3; striatum, n=3) and were perfused 24 hours later. To discriminate between retrograde transport of GFP protein and true infection of projecting neurons by retrogradely transported AAV viral particles, AAV particles conjugated to the fluorescent dye, Cy3, were injected into either the hippocampus or striatum. Previous work has shown that careful conjugation of this probe does not alter the infectivity of the virus.

To demonstrate that labeled virus was fully infectious, HEK 293 cells were infected with Cy3-AAV-GFP. Confocal microscopic analysis showed that virus attached to the cell membrane within minutes; by 30 minutes, virus had localized within the nucleus, and GFP expression could be observed by 24 hours.

Examination of entorhinodentate and nigrostriatal projection neurons 24 hours following in vivo delivery of Cy3-conjugated AAV to the hippocampus and striatum, respectively, revealed the presence of Cy3 particles within the cytoplasm and nucleus of these projection neurons. Systematic sampling of the labeled region revealed that 65% of substantia nigra pars compacta neurons and 90% of entorhinal layer II neurons contained Cy3-conjugated viral particles. Intraventricular delivery of the microtubule depolymerizing agent, colchicine, completely blocked the retrograde transport of Cy3-conjugated AAV particles at 24 hours after injection, demonstrating that viral particles were moved by specific retrograde axonal transport. Furthermore, adjacent, non-projecting glial cells did not contain Cy3-conjugated AAV particles, suggesting that retrograde transport of viral particles had occurred by such an intracellular mechanism.

Examination of entorhinodentate and nigrostriatal projection neurons 24 hours following in vivo delivery of Cy3-conjugated AAV to the hippocampus and striatum, respectively, revealed the presence of Cy3 particles within the cytoplasm and nucleus of these projection neurons. We also discovered that AAV viral particles conjugated to the fluorophore Cy3 (red) in a population of entorhinal layer II cells were detected by the DNA stain ToPro3 (blue) following injection to the ipsilateral dentate gyrus. By merging images in of the Cy3 conjugated AAV viral particles with images of the neuronal marker, NeuN, we showed that the viral particles were located within entorhinal neurons. Also, AAV-Cy3 tagged virus injected into the striatum were detected in cells of the ipsilateral substantia nigra. By detecting with tyrosine hydroxylase (TH, green) we revealed the presence of viral particles within TH-positive nigral neurons.

There was sparse labeling of projection neurons in those regions (medial septum, contralateral hippocampus) with limited GFP expression. Systematic sampling found that 65% of substantia nigra pars compacta neurons and 90% of entorhinal layer II neurons contained Cy3-conjugated viral particles. Adjacent, non-projecting glial cells did not contain Cy3-conjugated AAV particles, suggesting that retrograde transport of viral particles had occurred by specific intracellular means. Intraventricular delivery of the microtubule depolymerizing agent, colchicine, completely blocked the retrograde transport of Cy3-conjugated AAV particles at 24 hours after injection demonstrating that viral particles were moved by specific retrograde axonal transport.

4. Confirmation of Active Transcription of Reporter Gene in Projection Neurons

To determine if GFP was actively transcribed in the projection neurons, RT-PCR analysis was performed two weeks following AAV delivery to the hippocampus or striatum. This was accomplished in the following manner. Tissue from hippocampal (n=2) or striatal (n=2) rAAV-GFP injected animals was collected after two weeks using RNase free materials and reagents. RNA was isolated from both the injection sites and projection neuron populations, in addition to a control region (cerebellum). Total RNA was isolated from the tissue using the RNAzol B reagent (Tel-Test, Inc.). Reverse transcription was performed with the Superscript kit (Life Technologies) using oligo dT primer. For amplification, the 5' primer; GTGGATCCTGAGAACTTCAG (SEQ ID NO:1) was homologous to the 5' untranslated region of the rAAV-GFP transcript, while the 3' primer; AAGTCGT-GCTGCTTCATGTGG (SEQ ID NO:2) was homologous to GFP. These primers flank a human β-globin intron that is removed from the mRNA by splicing. Thirty cycles of PCR were performed (1 min. each at 94° C., 60° C., and 72° C.) using Taq DNA polymerase (Promega). PCR products were analyzed by electrophoresis on a 3% agarose gel. Amplification primers flanking an intervening sequence intron at the 5' end of the transcript were used to distinguish single stranded viral DNA from mRNA.

Amplification from single or double stranded viral genomic DNA generated a 900 base pair (bp) product in a control reaction using pAAV-GFP vector plasmid as the template, while mRNA processed to excise the intron yielded a 300 bp product. This RT-PCR analysis of viral expression revealed appropriate 300 bp transcripts in the substantia nigra of animals receiving striatal injections and in the entorhinal cortex of animals receiving hippocampal injections of AAV-GFP. At the site of injection, viral genomic DNA generated a 900 bp product in a control reaction using a pAAV-GFP vector plasmid.

Viral message was detected at high levels at the hippocampal and striatal injection sites of both animals, as well as at lower levels in the entorhinal cortex and substantia nigra. Viral genomic DNA was detected in both injection areas and faintly in one substantia nigra region. The viral transport studies and the RT-PCR data indicate that the virus was retrogradely transported from the injection sites, the recombinant viral genome was converted to double stranded DNA, mRNA was transcribed and spliced, and GFP was translated.

5. Expression of a Reporter Gene in Spinal Cord Neurons

Expression of the reporter gene is not limited to cranial neurons; the AAV vector is also capable of retrograde transport from an innervated muscle injection site into spinal motorneurons. Specifically, eAAV-EFGP (Enhanced Green Fluorescent Protein) was injected into the tibialis muscle of an adult mouse. Two weeks post injection, the muscle and spinal cord were evaluated for GFP expression. High level expression was found in the muscle and significant expression was found in the neurons of the spinal cord projected to the muscle. This indicates retrograde axonal transport of the virus within spinal motorneurons and demonstrates that the rAAV vector may be broadly employed in the retrograde infection of neurons throughout the CNS.

6. Use of rAAV-Mediated Retrograde Axonal Transport in Central Nervous System Mapping Infection, retrograde axonal transport, and stable expression of a reporter gene using a rAAV vector may be employed in order to conduct retrograde mapping of the central nervous system. In retrograde mapping, recombinant AAV vector bearing a reporter gene, such as the GFP gene employed in the examples above, may be delivered at the titers described above. Subsequent to delivery, the neurons projecting to the delivery field may be determined by the expression pattern of the reporter gene. In the examples above, GFP was employed, but such mapping is not limited to the use of this gene; other fluorescent markers may be employed, or alternatively, the presence of the marker may be assessed by staining or using immunological techniques.

The use of a rAAV vector in such mapping offers significant advantages over previous vectors capable of retrograde transport. As noted above, such vectors, such as recombinant herpes simplex virus and recombinant pseudorabies virus, are often toxic to the cells infected and may provoke an immune response. Such inflammatory responses are damaging to CNS tissue and may lead to errors in mapping. Furthermore, the integrative and stable nature of the AAV virus allows mapping to be conducted for a relatively long period of time after delivery of the viral vector; expression of the transgene has been reported for a period of months to years after transduction.

As noted above, the methods disclosed herein are not limited to the use of AAV vectors. Thus, other vectors that are substantially non-toxic, capable of retrograde transport, and enable stable, long-term gene expression may also be employed. Potential vectors of this type are lentivirus vectors and liposomal vectors.

7. Viral Delivery of Therapeutic Genes Via Retrograde Transport a. Alzheimer's Disease: Intrahippocampal Delivery of an Anti-Apoptotic Factor It is possible to deliver a therapeutic gene to a specific population of projection neurons using the methods described above. For example, as noted above, entorhinal layer II neurons suffer severe degeneration early in the progression of Alzheimer's disease. By transecting the perforant pathway in a rodent model, it is possible to produce selective degeneration of layer II entorhinal neurons, thus providing an animal model for the progression of Alzheimer's.

AAV containing the anti-apoptotic gene (Bcl-xL) and a GFP reporter (AAV-Bcl-xL) was injected into a rat hippocampus to determine if expression of Bcl-xL would protect entorhinal layer II neurons from subsequent injury. Injection was carried out as described above, and evaluation of the protective effects of the viral injection was assessed as follows. Two weeks following viral injection, half of the hippocampal-injected animals (AAV-GFP, n=6; AAV-Bcl-xL/GFP, n=6) received right-unilateral perforant path lesions. Quantification of entorhinal layer II neuron number was performed on a one in six series of propidium iodide stained sections for each animal using the optical fractionator procedure (MicroBrightField, Inc., Lokhester, Vt.). Statistical analysis was performed by multi-way ANOVA followed by a Bonferroni post-hoc analysis of means differences between groups (GraphPad Software, San Diego, Calif.).

Virally delivered Bcl-xL was produced as a fusion protein with GFP to permit detection and localization of infected cells, since it is not possible to discriminate by immunocytochemical detection between endogenous rodent Bcl-xL and the transfected Bcl-xL gene product. To demonstrate that the Bcl-xL/GFP fusion protein was functional, HEK293 cells were infected with either AAV-GFP or AAV-Bcl-xL/GFP. The HEK293 cells were then treated with staurosporine or tyrphostin, which are known to cause apoptosis. It was determined that only the Bcl-xL/GFP gene product successfully protected cells from staurosporine- or tyrphostin-induced apoptotic cell death.

Within two weeks following injection of AAV-Bcl-xl/GFP into the hippocampus, entorhinal layer II neurons showed expression of GFP in a distribution and intensity equivalent to that of animals treated with AAV-GFP. We found that entorhinal layer II projection neurons to the dentate gyrus formed a distinct band of cells in the uninjured entorhinal cortex. Projection neurons are large cells with an RNA-rich cytoplasm. Entorhinal neurons infected with the Bcl-xL/GFP construct were indistinguishable from cells infected by AAV-GFP alone in unlesioned animals. Layer II neurons appeared healthy after infection with either construct and quantitation revealed no cell loss following expression of the functional transgene, Bcl-xL in unlesioned animals.

Transfection of the perforant pathway produced significant death of entorhinal layer II neurons after two weeks in animals expressing only GFP, with over 60% loss of layer II neurons. However, quantitation of entorhinal layer II neurons showed no toxic effect of the Bcl-xL construct in unlesioned animals. Creating a perforant pathway lesion produced a significant 60% loss of GFP-expressing entorhinal neurons ($p<0.001$). In contrast, there were more than twice as many surviving neurons in animals that were first transfected with the AAV-Bcl-xL/GFP construct demonstrating significant protection by the Bcl-xL transgene ($p<0.01$). Surviving neurons still expressed GFP, but were shrunken and surrounded by apoptotic bodies and an increased population of glial cells. We also found that prior retrograde in vivo AAV gene delivery of the reporter gene, GFP, failed to protect vulnerable layer II neurons from subsequent lesion of the perforant pathway resulting in neuronal loss and atrophy of remaining neurons. Glial cell numbers were increased in response to injury and apoptotic bodies were seen in the cells transfected with the AAV-GFP construct. GFP was still expressed within surviving neurons. In contrast, expression of Bcl-xL protected entorhinal layer II neurons from the significant injury-induced death seen in animals transfected with the AAV-GFP construct. Entorhinal neurons appeared healthy and continued to express the Bcl-xl/GFP transgene. Thus, we found that in vivo, retrograde delivery of AAV-Bcl-xL/GFP protected entorhinal neurons from apoptosis due to a perforant pathway lesion. Individual entorhinal neurons appeared healthy and continued to express Bcl-xL/GFP. Despite neuronal sparing, there was still an increase in glial cell number. These data illustrate that expression of the anti-apoptotic gene, Bcl-xL, in targeted projection neurons will contribute to their survival following exposure to substantial injury.

b. Parkinson's Disease: Intrastriatal Delivery of an Apoptotic Factor

In one experiment we demonstrated that the AAV-GFP/Bcl-xL clone delivered to the striatum could protect against a Parkinson's Disease model. Adult rats were injected into the striatum with AAV-GFP/Bcl-xL, or saline as a control, two weeks prior to injection of 6-hydroxydopamine (6-OHDA), a specific neurotoxin to dopaminergic neurons within the substantia nigra pars compacta. Four weeks after delivery of 6-OHDA, the retrograde tracer fluorogold was injected into the striatum and animals were sacrificed 4 days later.

Nigral neurons were evaluated by fluorogold and TH immunohistochemistry. Quantification of nigral neurons within the substantia nigra pars compacta showed that normal, non-injected animals had approximately 13,000 fluorogold positive cells while the animal lesioned with 6-OHDA (n=1) and injected with saline (control) had 1,260 fluorogold positive cells. In contrast, the two animals that received AAV-GFP/Bcl-xL injections had 10,890 and 11,243 fluorogold positive cells indicating that retrograde delivery of AAV-GFP/Bcl-xL from the striatum to the nigra was protecting nigral-TH positive cells from being lesioned with 6-OHDA.

Similarly, other therapeutic genes, such as the Bcl-2 family of anti-apoptotic genes, can be packaged into such rAAV vectors (or other vectors such as the lentiviruses and liposomes described above to the extent such vectors are capable of retrograde transport) and employed to deliver these therapeutic genes to a person in order to treat Parkinson's and other diseases. For example, the Bcl-2 gene can be cloned into an AAV and transfected at high titer into the striatum to allow for retrograde transport and long-term transfection. Expression of Bcl-2 is then found, along with protection of the transfected cells against apoptosis.

c. ALS/Spinal Injury

In addition, as described above, a rAAV vector bearing a therapeutic gene, such as nerve growth factor or insulin-like growth factor I, can be injected into a person at the high titers described above into a muscle innervated by a spinal motorneuron affected by a neurodegenerative disease such as ALS or by a spinal cord injury. Subsequent retrograde transport of the virus can be used to deliver the therapeutic transgenes to the spinal cord. Such methods may be used in treating amyotrophic lateral sclerosis (ALS), spinal motorneuron diseases, and spinal cord injury.

d. Blocking Signaling and Antisense

Furthermore, rAAV vector bearing an antisense gene may be employed in order to inhibit activity in a neuron. Such applications may be of use, for example, in ameliorating calcium toxicity when Ca-binding proteins are overexpressed and lead to the sequestering of calcium in neurons or when antisense vectors against particular receptors, such as glutamate receptors, are used to eliminate or decrease receptor numbers.

Furthermore, the therapeutic methods described above are not limited to the genes described; other genes, such as those encoding FGF proteins, NT-3, neurotrophic factors such as BDNF and GDNF (see, e.g., Yuen EC, Phys Med Rehabil Clin N Am. (2001) 12(2):293–306, viii), or any gene which may be of therapeutic interest when retrogradely transported and expressed, may be employed. This approach could involve, for example, both the delivery of the gene encoding tyrosine hydroxylase to boost dopamine production or the delivery of genes encoding neurotrophic factors such as GDNF to promote the survival of dopaminergic neurons.

Although the foregoing description of the invention has shown, described and pointed out novel features of the invention, it will be understood that various omissions, substitutions, and changes in the form of the detail of the apparatus as illustrated, as well as the uses thereof, may be made by those skilled in the art without departing from the spirit of the present invention. Consequently the scope of the invention should not be limited to the foregoing discussion but should be defined by the following claims.

What is claimed is:

1. A method for transducing a human neuron with a heterologous gene, wherein said human neuron has a synaptic portion and a cellular portion, comprising:
providing at least $1.5 \times 10^7$ infectious particles of an adeno-associated viral vector comprising a heterologous gene to be transduced into a human neuron; and
contacting the synaptic portion of said human neuron with said viral vector under conditions whereby said contacting results in transduction of the viral vector into said synaptic portion, and retrograde movement of said viral vector from the synaptic portion to the cellular portion, wherein said heterologous gene is incorporated into the genome of the human neuron and expressed by said human neuron for at least two months.

2. The method of claim 1, where said viral vector exhibits tropism toward human neurons.

3. The method of claim 1, wherein said method is performed in vivo.

4. The method of claim 1, wherein at least $1.5 \times 10^8$ infectious particles of said viral vector are provided.

5. The method of claim 1, wherein at least $1.5 \times 10^9$ infectious particles of said viral vector are provided.

6. The method of claim 1, wherein said gene is further expressed by said human neuron for at least four months.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: 5' primer to an intron of human beta-globin
```

```
<400> SEQUENCE: 1
gtggatcctg agaacttcag                                                    20

<210> SEQ ID NO 2
<211> LENGTH: 21
<212> TYPE: DNA
<213> ORGANISM: Artificial Sequence
<220> FEATURE:
<223> OTHER INFORMATION: 3' primer to an intron of human beta-globin

<400> SEQUENCE: 2
aagtcgtgct gcttcatgtg g                                                  21
```